United States Patent
Scheiner et al.

(10) Patent No.: US 6,584,362 B1
(45) Date of Patent: Jun. 24, 2003

(54) LEADS FOR PACING AND/OR SENSING THE HEART FROM WITHIN THE CORONARY VEINS

(75) Inventors: Avram Scheiner, Vadnais Heights, MN (US); Ronald W. Heil, Jr., Roseville, MN (US); Peter T. Kelley, Buffalo, MN (US); Bruce Tockman, Scandia, MN (US); Randy Westlund, Minneapolis, MN (US); Jay A. Warren, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 23 days.

(21) Appl. No.: 09/651,340

(22) Filed: Aug. 30, 2000

(65) Prior Publication Data (65)

(51) Int. Cl.⁷ .................................................. A61N 1/05
(52) U.S. Cl. ....................................... 607/122; 607/125
(58) Field of Search .......................... 60/372–375, 377, 60/381, 393; 607/115, 116, 119, 122–123, 126, 125

(56) References Cited

U.S. PATENT DOCUMENTS

| | | | |
|---|---|---|---|
| 3,835,864 A | 9/1974 | Rasor et al. | 128/419 P |
| 3,943,936 A | 3/1976 | Rasor et al. | 128/419 P |
| 4,122,294 A | 10/1978 | Frolov | 13/18 |
| RE30,366 E | 8/1980 | Rasor et al. | 128/419 P R |
| 4,332,259 A | 6/1982 | McCorkle, Jr. | 128/786 |

(List continued on next page.)

FOREIGN PATENT DOCUMENTS

| | | | |
|---|---|---|---|
| DE | 20010369 | 8/2000 | A61N/1/05 |
| EP | 0488512 | 10/1990 | |
| EP | 0951920 | 10/1999 | A61N/1/05 |
| EP | 1013303 | 6/2000 | A61N/1/05 |

Primary Examiner—Kennedy Schaetzle
Assistant Examiner—Kristen Droesch
(74) Attorney, Agent, or Firm—Schwegman, Lundberg, Woessner & Kluth, P.A.

(57) ABSTRACT

A lead for monitoring or stimulating cardiac activity is provided. The lead is adapted for implantation on or about the heart within the coronary vasculature and for connection to a signal generator. The lead body has one or more electrodes associated therewith. The lead is constructed and arranged so that when it is implanted, the electrodes are housed in the coronary vasculature and urged into intimate contact a vessel wall. A method for implanting the lead into the coronary vasculature is also provided, the method comprising the steps of inserting a stylet into the lead, inserting the lead into the coronary sinus, advancing the lead from the coronary sinus toward the toward the left atrium and into a coronary vein, removing the stylet, and sensing and pacing the heart. Alternatively, the method comprises placing a guide catheter into the coronary sinus, threading a guide wire into the coronary veins, pushing the lead over the guide wire and into the coronary sinus or the coronary vein, and sensing and pacing the heart via the lead in its implanted site in the coronary sinus or the coronary vein.

6 Claims, 14 Drawing Sheets

U.S. PATENT DOCUMENTS

| | | | |
|---|---|---|---|
| 4,399,818 A | 8/1983 | Money | 128/419 PG |
| 4,402,330 A | 9/1983 | Lindemans | 128/786 |
| 4,408,608 A | 10/1983 | Daly et al. | 128/421 |
| 4,458,677 A | 7/1984 | McCorkle, Jr. | 128/786 |
| 4,577,639 A | 3/1986 | Simon et al. | 128/709 |
| 4,592,359 A | 6/1986 | Galbraith | 128/419 R |
| 4,665,925 A | 5/1987 | Millar | 128/663 |
| 4,889,128 A | 12/1989 | Millar | 128/662.06 |
| 4,928,688 A | 5/1990 | Mower | 128/419 PG |
| 4,932,407 A | 6/1990 | Williams | 128/419 D |
| 4,957,111 A | 9/1990 | Millar | 128/662.06 |
| 4,958,632 A | 9/1990 | Duggan | 128/419 PG |
| 5,014,696 A | 5/1991 | Mehra | 128/419 D |
| 5,076,272 A | 12/1991 | Ferek-Petric | 128/419 |
| 5,099,838 A | 3/1992 | Bardy | 128/419 D |
| 5,144,960 A | 9/1992 | Mehra et al. | 128/786 |
| 5,165,403 A | 11/1992 | Mehra | 128/419 D |
| 5,167,229 A | 12/1992 | Peckham et al. | 128/421 |
| 5,226,427 A | 7/1993 | Buckberg et al. | 128/772 |
| 5,277,231 A | 1/1994 | Dostalek | 140/106 |
| 5,308,356 A | 5/1994 | Blackshear, Jr. et al. | 606/194 |
| 5,318,593 A | 6/1994 | Duggan | 607/9 |
| 5,331,966 A | 7/1994 | Bennett et al. | 128/696 |
| 5,372,125 A | 12/1994 | Lyons | 128/64 D |
| 5,387,233 A * | 2/1995 | Alferness et al. | 607/122 |
| 5,405,374 A | 4/1995 | Stein | 607/122 |
| 5,409,469 A | 4/1995 | Schaerf | 604/282 |
| 5,411,524 A | 5/1995 | Rahul | 607/4 |
| 5,423,806 A | 6/1995 | Dale et al. | 606/15 |
| 5,441,504 A | 8/1995 | Pohndorf et al. | 606/129 |
| 5,465,715 A | 11/1995 | Lyons | 128/640 |
| 5,476,498 A * | 12/1995 | Ayers | 607/122 |
| 5,540,727 A | 7/1996 | Tockman et al. | 607/18 |
| 5,545,204 A * | 8/1996 | Cammilli et al. | 600/374 |
| 5,549,642 A | 8/1996 | Min et al. | 607/5 |
| 5,578,069 A | 11/1996 | Miner, II | 607/126 |
| 5,609,621 A | 3/1997 | Bonner | 607/122 |
| 5,639,276 A | 6/1997 | Weinstock et al. | 606/129 |
| 5,674,217 A | 10/1997 | Wahlstrom et al. | 606/15 |
| 5,683,445 A | 11/1997 | Swoyer | 607/125 |
| 5,700,283 A | 12/1997 | Salo | 607/17 |
| 5,704,351 A | 1/1998 | Mortara et al. | 128/630 |
| 5,713,867 A | 2/1998 | Morris | 604/164 |
| 5,720,768 A | 2/1998 | Verboven-Nelissen | 607/9 |
| 5,744,038 A | 4/1998 | Cham | 210/634 |
| 5,755,761 A | 5/1998 | Obino | 607/122 |
| 5,755,766 A | 5/1998 | Chastain et al. | 607/122 |
| 5,769,875 A | 6/1998 | Peckham et al. | 607/48 |
| 5,772,693 A | 6/1998 | Brownlee | 607/123 |
| 5,776,073 A | 7/1998 | Garfield et al. | 600/546 |
| 5,776,171 A | 7/1998 | Peckham et al. | 607/48 |
| 5,782,879 A | 7/1998 | Rosborough et al. | 607/6 |
| 5,800,495 A | 9/1998 | Machek et al. | 607/116 |
| 5,803,928 A | 9/1998 | Tockman et al. | 607/122 |
| 5,814,088 A | 9/1998 | Paul et al. | 607/28 |
| 5,824,032 A | 10/1998 | Belden | 607/126 |
| 5,843,117 A | 12/1998 | Alt et al. | 606/194 |
| 5,871,529 A | 2/1999 | Bartig et al. | 607/122 |
| 5,871,531 A | 2/1999 | Struble | 607/126 |
| 5,897,577 A | 4/1999 | Cinbis et al. | 607/28 |
| 5,902,324 A | 5/1999 | Thompson et al. | 607/9 |
| 5,913,887 A | 6/1999 | Michel | 607/123 |
| 5,922,014 A | 7/1999 | Warman et al. | 607/123 |
| 5,925,073 A | 7/1999 | Chastain et al. | 607/122 |
| 5,931,864 A | 8/1999 | Chastain et al. | 607/128 |
| 5,935,160 A * | 8/1999 | Auricchio et al. | 607/122 |
| 5,954,758 A | 9/1999 | Peckham et al. | 607/48 |
| 5,978,707 A | 11/1999 | Krig et al. | 607/14 |
| 5,983,138 A | 11/1999 | Kramer | 607/9 |
| 6,006,137 A | 12/1999 | Williams | 607/119 |
| 6,014,581 A | 1/2000 | Whayne et al. | 600/523 |
| 6,021,354 A | 2/2000 | Warman et al. | 607/123 |
| 6,026,328 A | 2/2000 | Peckham et al. | 607/48 |
| 6,027,462 A | 2/2000 | Greene et al. | 600/585 |
| 6,049,732 A | 4/2000 | Panescu et al. | 600/523 |
| 6,055,457 A | 4/2000 | Bonner | 607/126 |
| 6,070,104 A | 5/2000 | Hine et al. | 607/123 |
| RE36,765 E | 7/2000 | Mehra | 607/4 |
| 6,106,460 A | 8/2000 | Panescu et al. | 600/300 |
| 6,112,117 A | 8/2000 | KenKnight et al. | 607/5 |
| 6,115,626 A | 9/2000 | Whayne et al. | 600/427 |
| 6,129,750 A | 10/2000 | Tockman et al. | 607/125 |
| 6,132,456 A | 10/2000 | Sommer et al. | 607/127 |
| 6,148,233 A | 11/2000 | Owen et al. | 607/5 |
| 6,159,237 A | 12/2000 | Alt et al. | 623/1.11 |
| 6,161,029 A * | 12/2000 | Spreigl et al. | 600/375 |
| 6,163,725 A | 12/2000 | Peckham et al. | 607/61 |
| 6,377,856 B1 * | 4/2002 | Carson | 607/122 |

* cited by examiner

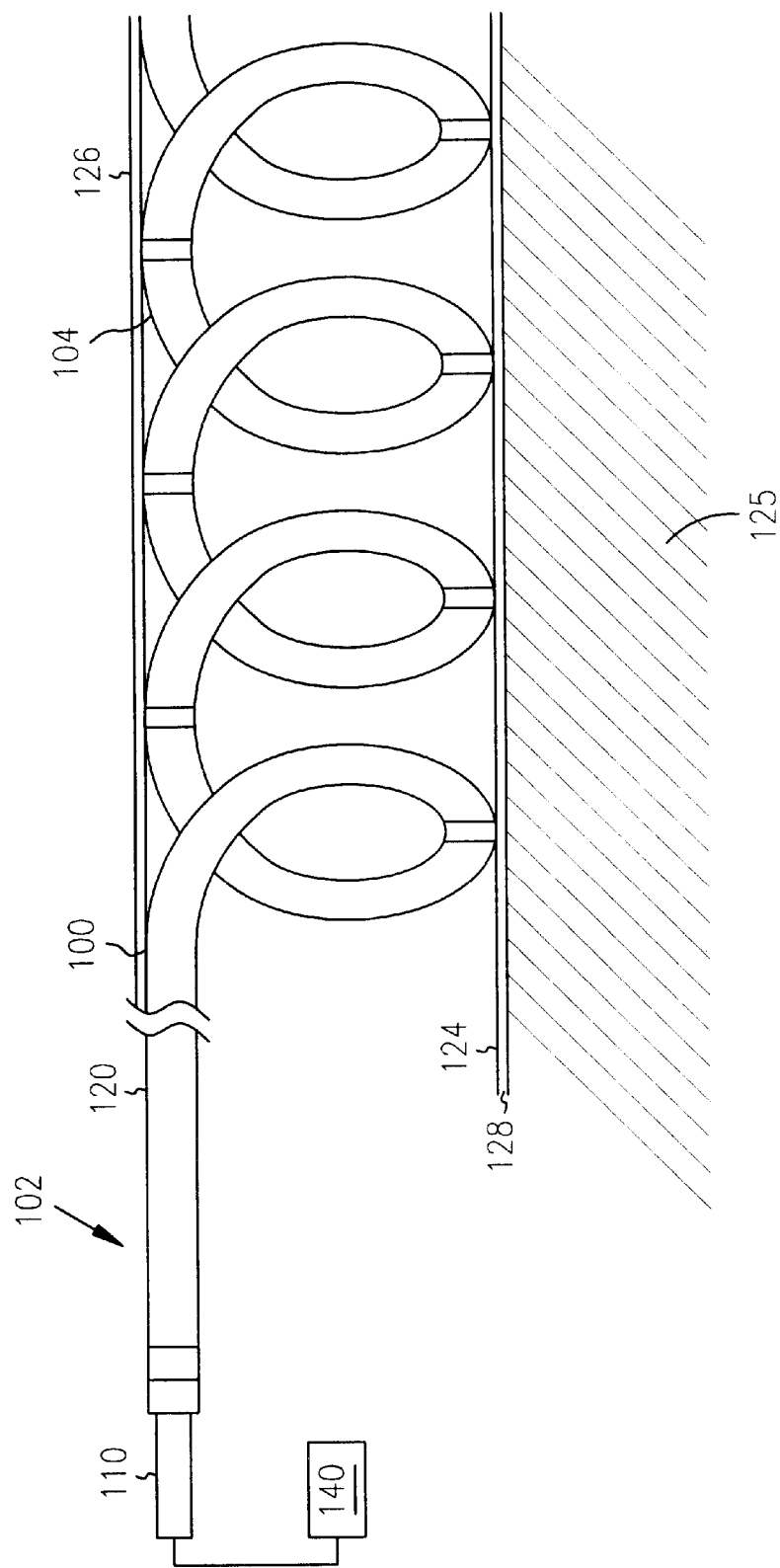

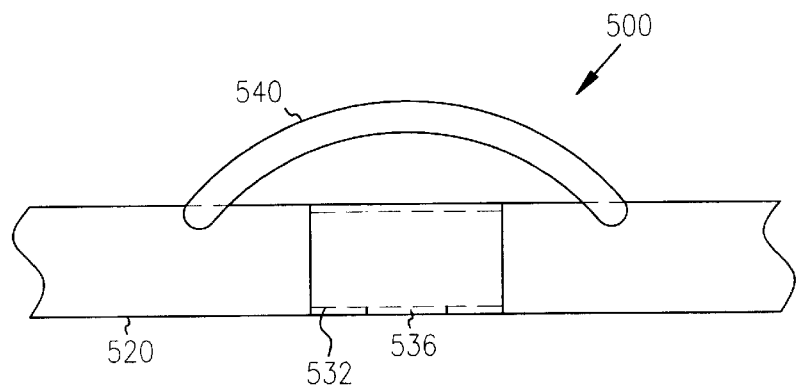
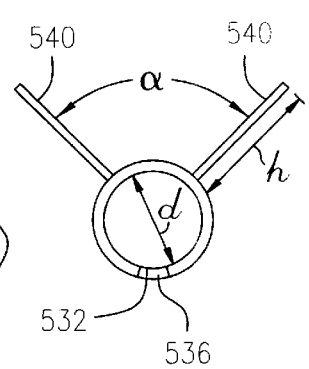
FIG. 5A      FIG. 5B
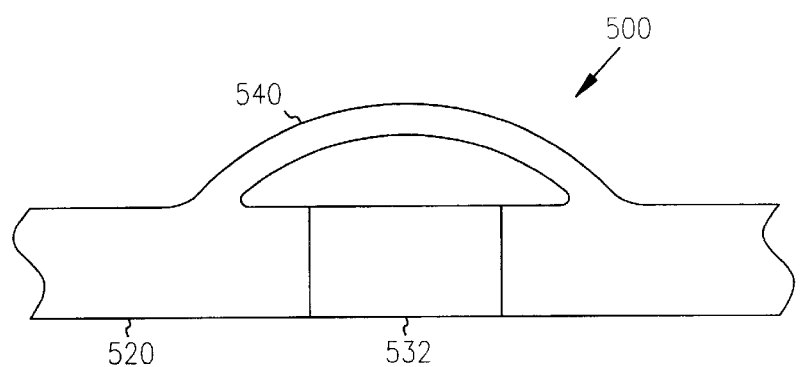
FIG. 5C
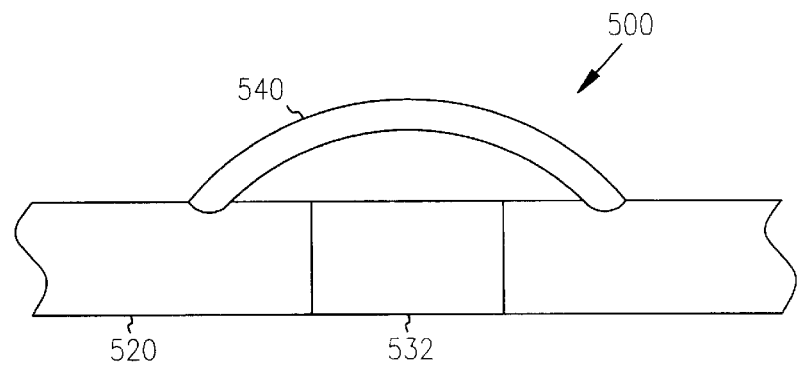
FIG. 5D

LEADS FOR PACING AND/OR SENSING THE HEART FROM WITHIN THE CORONARY VEINS

CROSS-REFERENCE TO RELATED APPLICATIONS

This application is related to co-pending, commonly assigned U.S. patent application Ser. No. 09/650,568 entitled "SITE REVERSION IN CARDIAC RHYTHM MANAGEMENT" filed even date herewith, the specification of which is hereby incorporated by reference.

TECHNICAL FIELD

The present invention relates to the field of leads for correcting arrhythmias of the heart. More particularly, this invention relates to leads for pacing and/or sensing the heart from the coronary vasculature.

BACKGROUND OF THE INVENTION

A cardiac pacing system includes a battery powered pulse generator and one or more leads for delivering pulses to the heart. Current pulse generators include electronic circuitry for determining the nature of an irregular rhythm, commonly referred to as arrhythmia, and for timing the delivery of a pulse for a particular purpose. The pulse generator is typically implanted into a subcutaneous pocket made in the wall of the chest. Insulated wires called leads attached to the pulse generator are routed subcutaneously from the pocket to the shoulder or neck where the leads enter a major vein, usually the subclavian vein. The leads are then routed into the site of pacing, usually a chamber of the heart. The leads are electrically connected to the pulse generators on one end and are electrically connected to the heart on the other end. Electrodes on the leads provide the electrical connection of the lead to the heart. The leads deliver the electrical discharges from the pulse generator to the heart.

The electrodes are typically arranged on a lead body in two ways or categories. A pair of electrodes which form a single electrical circuit (i.e., one electrode is positive and one electrode is negative) positioned within the heart is a bipolar arrangement. The bipolar arrangement of electrodes requires two insulated wires positioned within the lead. When one electrode is positioned in or about the heart on a lead and represents one pole and the other electrode representing the other pole is the pulse generator, this arrangement is known as a unipolar arrangement. The unipolar arrangement of electrodes requires one insulated wire positioned within the lead.

Some patients require a pacing system having multiple sites in one chamber of the heart for detecting and correcting an abnormal heartbeat. In the past, a common practice for a patient requiring multi-site pacing within one or more chambers of the heart, would be to provide two separate and different leads attached to the particular chamber of the heart. One lead would be implanted at one site in the chamber. Another lead would be implanted at another site in the same chamber, or another chamber. Typically, the single chamber of the heart receiving multi-site pacing would be the right atrium.

Having two separate leads is undesirable for many reasons. Among these are the complexity of and time required for the implantation procedure for implanting two leads as compared to that of the procedure for implanting one lead. In addition, two leads may mechanically interact with one another after implantation which can result in dislodgement of one or both of the leads. In vivo mechanical interaction of the leads may also cause abrasion of the insulative layer along the lead which can result in electrical failure of one or both of the leads. Another problem is that as more leads are implanted in the heart, the ability to add leads is reduced. If the patient's condition changes over time, the ability to add leads is restricted. Two separate leads also increase the risk of infection and may result in additional health care costs associated with re-implantation and follow-up.

It is well understood that the heart functions with two sides. The right side of the heart receives blood from the body and pumps it into the lungs to exchange gases. The left side of the heart receives the oxygenated blood from the heart and pumps it to the brain and throughout the body. As currently practiced, endocardial pacing and defibrillation leads are positioned within the right chambers of the heart. A major reason that this is typically practiced is that the risk of severe cerebral accidents during endocardial, left heart procedures is greater than that encountered during endocardial right side heart procedures. Although it is safer for the patient to position leads within the right heart, numerous difficulties are encountered when it is desired to sense and pace the left heart endocardially.

There is a need for an endocardial lead that can reliably perform pacing and sensing of the heart without being placed in the left side of the heart.

SUMMARY

A lead is provided which includes a lead body adapted to carry signals to and from a heart, where the lead body has a proximal portion and a distal portion. The lead further includes a connector located at a proximal end of the lead. The lead is adapted for connection to a signal generator for monitoring or stimulating cardiac activity, and is constructed and arranged for implantation within a coronary vein. A portion of the distal portion of the lead body has a preformed radius of curvature substantially the same as or slightly smaller than a coronary sinus and geometrically shaped to hug a wall of the coronary sinus upon implantation therein. In addition, the lead further includes at least one electrode coupled with the lead body.

Several options for the lead are as follows. For example, the lead is constructed and arranged for implantation within the coronary sinus. In another option, the at least one electrode includes a first electrode associated with the distal portion of the lead body, and the first electrode includes a first electrode contact area. The at least one electrode further includes a second electrode associated with the distal portion of the lead body, and the second electrode includes a second electrode contact area. The distal portion of the lead is constructed and arranged to urge the first and second electrodes toward a wall of the coronary sinus. In yet a further option, the first electrode and the second electrode are spaced in close proximity to one another. Optionally, the lead further comprises at least one atrial pacing electrode. In yet another option, the distal portion of the lead body further includes a helical portion having the at least one electrode thereon, and the helical portion is constructed and arranged to urge the at least one electrode toward a myocardial wall. In a further option, the distal portion of the lead body further includes at least one arched tine located opposite the first electrode, and at least one arched tine located opposite the second electrode, where the tines are constructed and arranged to urge the electrode contact area of the first and second electrodes toward a myocardial wall of the coronary sinus. In another option, the distal portion of the lead body further comprises a double bias configuration constructed and arranged to urge the at least one electrode toward a myocardial wall of the coronary sinus. Other options include an external steroid collar disposed in close proximity to one electrode, or at least a portion of the lead body having a shape memory material. Still further, a distal portion of the lead body optionally has a tapered outer diameter.

In another embodiment, a lead is provided which includes a lead body adapted to carry signals to and from a heart, where the lead body has a proximal portion and a distal portion. The lead further includes a connector located at a proximal end of the lead. The lead is adapted for connection to a signal generator for monitoring or stimulating cardiac activity, and is constructed and arranged for implantation within a coronary vein. The distal portion of the lead body has a helical portion adapted to be implanted within a coronary vein. At least one electrode coupled with the helical portion of the lead body. Optionally, a plurality of electrodes are disposed on the helical portion, and the plurality of electrodes are spaced about 120 degrees apart along the helical portion.

Other optional features are as follows. For instance, the lead further includes apical electrodes, mid ventricular electrodes, and ventricular electrodes on the helical portion. In another example, at least a portion of the lead body comprises a shape memory material.

In yet another embodiment, a lead is provided which includes a lead body adapted to carry signals to and from a heart, where the lead body has a proximal portion and a distal portion, and an intermediate portion therebetween. The lead further includes a connector located at a proximal end of the lead. The lead is adapted for connection to a signal generator for monitoring or stimulating cardiac activity, and is constructed and arranged for implantation within a coronary vein. At least one electrode is coupled with the lead body. In addition, the distal portion of the lead body has a tapered outer diameter, and the outer diameter includes a first diameter at the intermediate portion and a second diameter at the distal portion, and the first diameter is greater than the second diameter.

Several options for the lead are as follows. For instance, the distal portion of the lead body further includes a helical portion which has the at least one electrode thereon, and the helical portion constructed and arranged to urge the at least one electrode toward a myocardial wall. As a further option, a plurality of electrodes are disposed on the helical portion, and the plurality of electrodes are spaced about 120 degrees apart along the helical portion. In yet another option, the lead further comprises apical electrodes, mid ventricular electrodes, and ventricular electrodes coupled with the lead body. Another example of an option is the distal portion of the lead body further includes at least one arched tine located opposite the at least one electrode. In yet another option, the at least one arched tine comprises a pliable, thin arched tine which extends from a first end to a second end, and the first end and the second end are coupled with the lead body.

A method for a cardiac vein lead is also described herein. The method includes providing any of the above coronary vein leads, inserting the coronary vein lead into the coronary sinus, advancing the lead from the coronary sinus toward the left atrium, and rotating the coronary vein lead. Optionally, the method further includes sensing and/or pacing the heart via the coronary vein lead.

In another method embodiment, a method includes providing any of the above coronary vein leads, where the coronary vein lead includes two or more electrodes, inserting the coronary vein lead into the coronary sinus, advancing the lead from the coronary sinus toward the left atrium. In one option, the method includes inserting a stylet into the coronary vein lead prior to inserting the coronary vein lead into the coronary sinus, and removing the stylet after inserting the coronary vein lead into the coronary sinus. In yet another option, the method further includes advancing the lead from the coronary sinus toward the left atrium and into a coronary branch vein. Another option includes pacing and sensing only the left atrium and/or the left ventricle.

In another method embodiment, a method includes providing any of the above coronary vein leads, where the coronary vein lead includes two or more electrodes, inserting the coronary vein lead into the coronary sinus, advancing the lead from the coronary sinus toward the left atrium. In one option, the method further includes placing a guide catheter into the coronary sinus, threading a guide wire into the coronary vein, and pushing the lead over the guide wire and into the coronary vein. In yet another option, the method further comprises hugging an interior wall of the coronary vein with the lead body.

In another method embodiment, a method includes providing any of the above coronary vein leads, where the coronary vein lead includes two or more electrodes, inserting the coronary vein lead into the coronary sinus, advancing the lead from the coronary sinus toward the left atrium. In one option, the method further comprises placing a guide catheter into the coronary sinus, threading a guide wire into the coronary sinus, pushing the coronary sinus lead over the guide wire and into the coronary sinus; and providing left sided sensing and pacing of the heart via the coronary sinus lead in its implanted site in the coronary sinus.

The leads advantageously provide the ability to sense and pace the heart using leads positioned within the cardiac vasculature, and further the leads provide the ability to pace and/or sense the left heart. It has been found that by placing a therapeutic lead near the atrium, but not in the atrium, higher amplitude electrograms may be detected as compared to a standard endocardial lead. Further, it has been found that left sided pacing may help suppress atrial arrhythmias, particularly those originating near the left atrium. Still further, it has been found that the ability to critically control the timing between pacing the atria and ventricles of the heart is of utility in optimizing pacing therapies. The leads described herein involve geometries that utilize the shape of the local vasculature, the shape of the heart, or both, to help insure that an optimally positioned lead will remain in that position well beyond the time of implant. The lead designs discussed herein yield reliable and optimal performance in sensing and pacing of the heart. New coronary lead configurations are provided which can provide dual chamber pacing and/or defibrillation on a single lead body.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE FIGURES

FIG. 1B is a side view of a coronary vein lead constructed in accordance with another embodiment;

FIG. 5A is a side view of a portion of a coronary vein lead constructed in accordance with one embodiment;

FIG. 5B is an end view of a coronary vein lead constructed in accordance with one embodiment;

FIG. 5C is a side view of a portion of a coronary vein lead constructed in accordance with one embodiment;

FIG. 5D is a side view of a portion of a coronary vein lead constructed in accordance with one embodiment;

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1A:
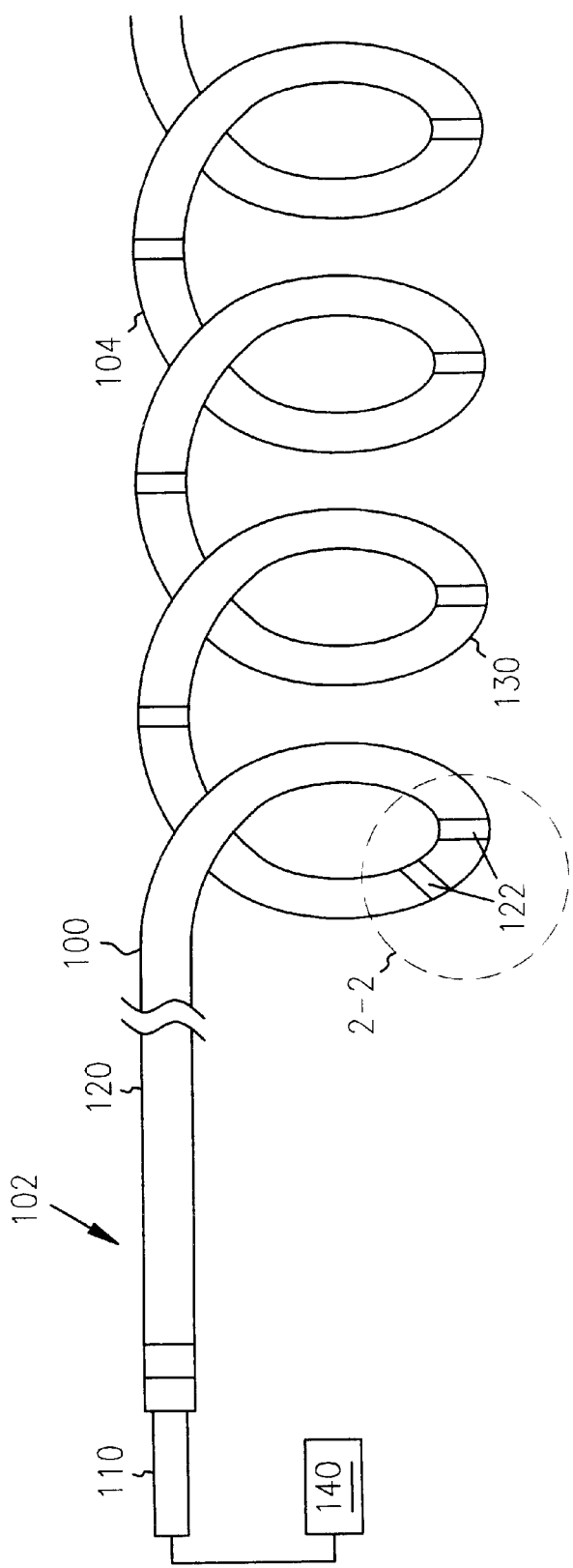
FIG. 1A is a side view of a coronary vein lead constructed in accordance with one embodiment.

FIG. 1A is a side view of one example of a coronary vein lead 100. The lead 100 has a proximal end 102 and a distal end 104 and includes a connector terminal 110 and a lead body 120. The lead 100 attaches to a pulse sensor and generator 140. In one embodiment, the lead 100 is constructed and arranged for insertion into the coronary sinus, as discussed further below. The lead body 120 has a number of electrodes 122 in its distal end 104 which is implanted in a coronary vein. The connector terminal 110 electrically connects the various electrodes and conductors within the lead body 120 to a pulse sensor and generator 140. The pulse sensor and generator 140 contains electronics to sense various pulses of the heart and also produce pulsing signals for delivery to the heart. The pulse sensor and generator 140 also contains electronics and software necessary to detect certain types of arrhythmias and to correct for them.

The lead 100, in one option, operates similarly to a bipolar lead having positive and negative portions of a circuit located in the lead body 120. It should be noted that this lead may also be made a unipolar lead. In other words, one electrode or both electrodes of the lead body 120 can be pacing/sensing electrodes, or one electrode can be a pacing/sensing electrode and the anode can be the pulse generator.

The lead body 120 is a tubing material formed from a polymer biocompatible for implantation, and preferably the tubing is made from a silicone rubber polymer. Alternatively, the lead body 120 may be made of a biocompatible material having shape memory characteristics such that it will return to its preformed shape once implanted and a stylet or guidewire is removed. An example of such a material is polyether polyurethane. In addition, the lead body 120 optionally has portions which have shape memory characteristics, comprising either a shape memory polymer or a shape memory metal. The lead body contains several electrical conductors. The electrical conductors are made of a highly conductive, highly corrosion-resistant material. The electrical conductors carry current and signals between the pulse sensor and generator 140 and the electrodes located at the distal end 104 of the lead 100. Electrical conductors are shown, for example, at 472 and 473 of FIGS. 4B and 4C, and at 672 and 673 of FIGS. 6C, 6E and 6G.

The lead body 120 optionally has a helical portion 130 at the distal end 104. After implantation, the helical portion 130 will be located in a coronary vein, as shown, for example, in FIG. 1B. Referring to FIG. 1B, a coronary vein 124 is shown which includes a free wall 126 and a myocardial wall 128. The free wall 126 is disposed away from the heart 125, and the myocardial wall 128 abuts the heart 125.

The helical portion 130 of the lead body 120 is optionally made of a biocompatible material having shape memory characteristics such that it will return to its preformed helical shape once implanted and a stylet or guidewire is removed. An example of such a material is polyether polyurethane. In addition, the lead body may have portions which have shape memory characteristics, comprising either a shape memory polymer or a shape memory metal. The diameter of the helical portion is about 0.25 cm–2 cm. The pitch of the helix ranges from 0.5 cm–2.5 cm. As mentioned above, the helical portion 130 includes electrodes 122. In one option, the electrodes 122 are evenly spaced at about 120 degrees apart, which increases the opportunity for the electrodes 122 to make contact with the myocardial wall 128. In a further option, pairs of electrodes 122 are evenly spaced about 120 degrees apart along the lead body 120. The electrodes 122 are electrically coupled with one conductor, or are electrically coupled with separate conductors.

The helical portion 130 facilitates placement of the electrodes against the myocardial wall 128 of the coronary vein 124 during and/or after implantation. The helical shape of the lead 100 provides large lead/vessel wall area interface to produce reliable, long term stability. When implanted, the helical shape of the lead 100 produces subtle lateral forces between the electrodes 122 and myocardial wall 128, resulting in low pacing thresholds.

Figure 2:
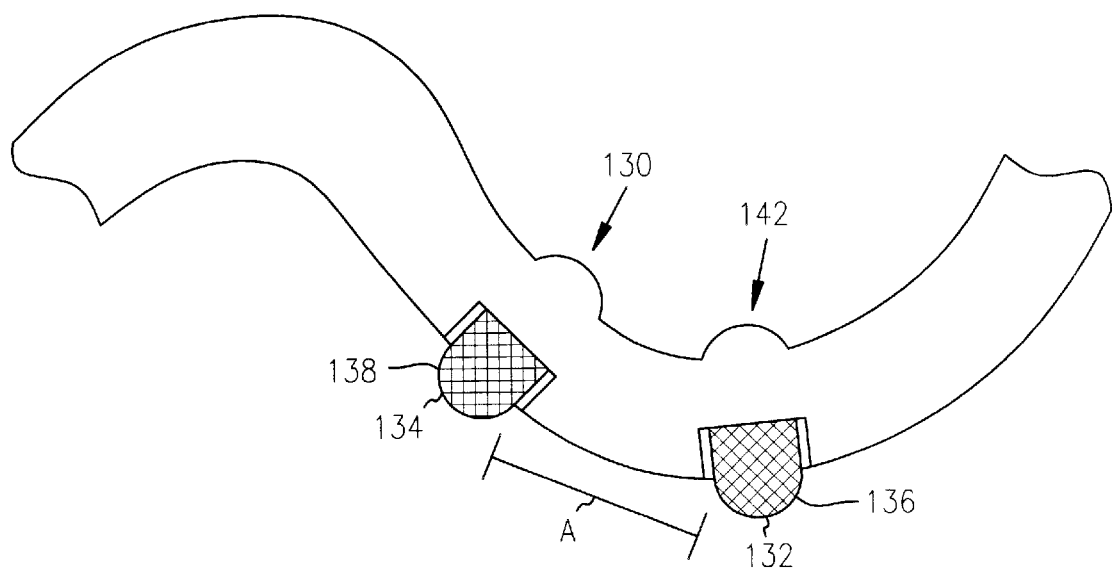
FIG. 2 is an enlarged view of the lead of FIG. 1A, taken along circle 2—2 of FIG. 1.

Referring to FIGS. 1A and 2, the distal end 104 of the lead 100 includes several electrodes 122, and in one example has two electrodes 132, 134. The first electrode 132 is generally referred to as the distal electrode. A second electrode 134 is located near the distal electrode and proximally thereof and can be used as a counter electrode for electrode 132 or for defibrillation therapy. The lead 100 may be generally described as a tachycardia (tachy) lead, although it is not limited thereto. The electrodes 132, 134 are of an electrically conductive material such as an alloy of platinum and iridium which is highly conductive and highly resistant to corrosion. The electrodes 132, 134 optionally include a passive fixation portion. Electrodes 132 and 134 are masked or otherwise insulated on the inside radius 142 of the distal end 104 of the lead 100. This decreases electrode area and provides desired increase in impedance. The bipolar electrode pair spacing between electrodes 132 and 134 is shown at line A of FIG. 2 to be from about 1–5 mm. With such close electrode spacing, increased rejection of problematic far field (ventricular) signals is accomplished. Optionally, the electrode surfaces 136, 138 are raised beyond the body 120 of the lead 100. Electrodes designed in this fashion increase the chances of achieving intimate tissue-electrode contact thereby resulting in lower thresholds.

Figure 3A:
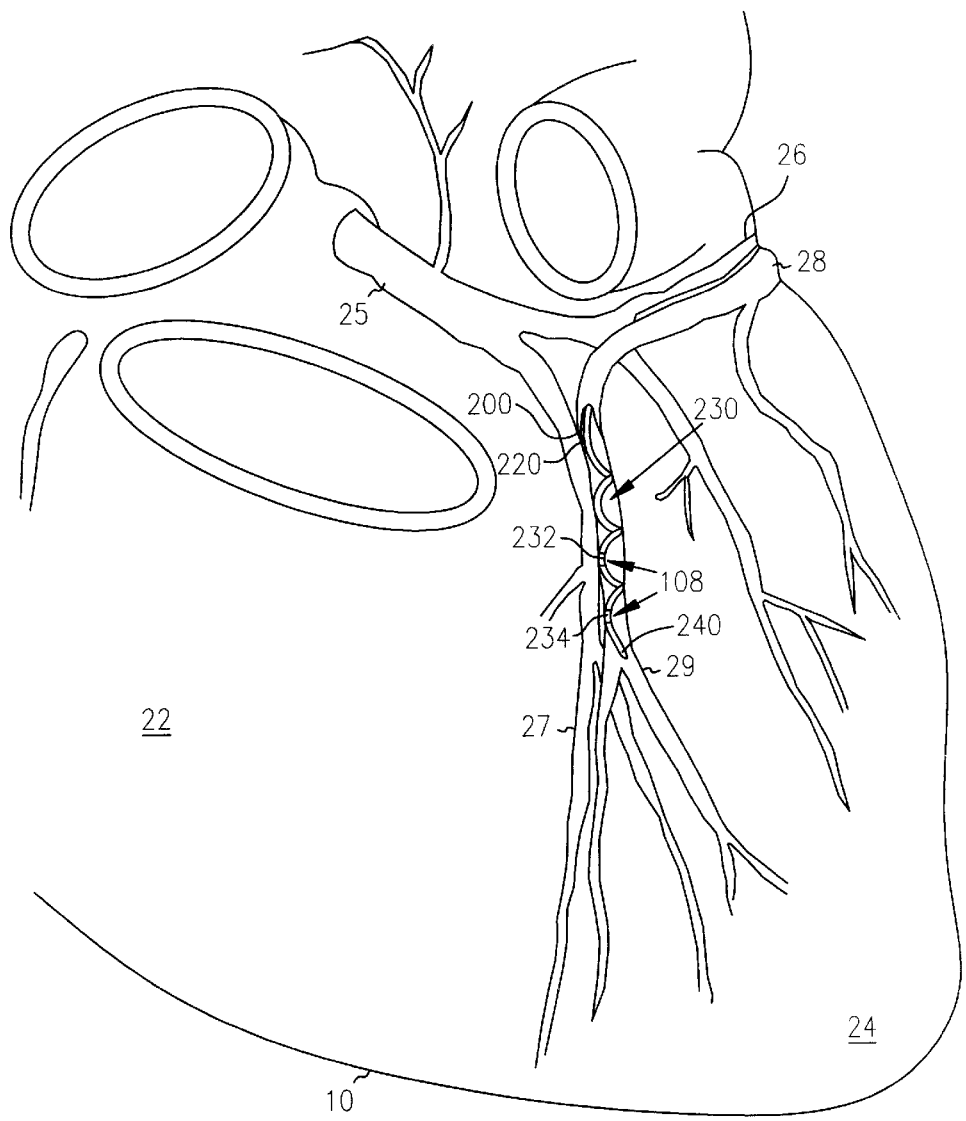
FIG. 3A is side view of a coronary vein lead constructed in accordance with one embodiment, shown positioned in a coronary vein.

FIG. 3A shows an alternative embodiment of a coronary vein lead 200 which has a helical distal end 230, where the heart 10, left ventricle 22, right ventricle and apex 24 of the heart 10 are shown. It should be noted that the helical distal end 230 can be combined with any of the embodiments discussed below. The left coronary artery 25 branches into the circumflex artery 26 and the anterior descending artery 27. The coronary sinus 28 branches into the coronary branch vein 29. Placing the lead 200 in the coronary branch veins, for example, on the left ventricle has been found to be a suitable means for delivering pacing therapy to patients suffering from congestive heart failure.

Figure 3B:
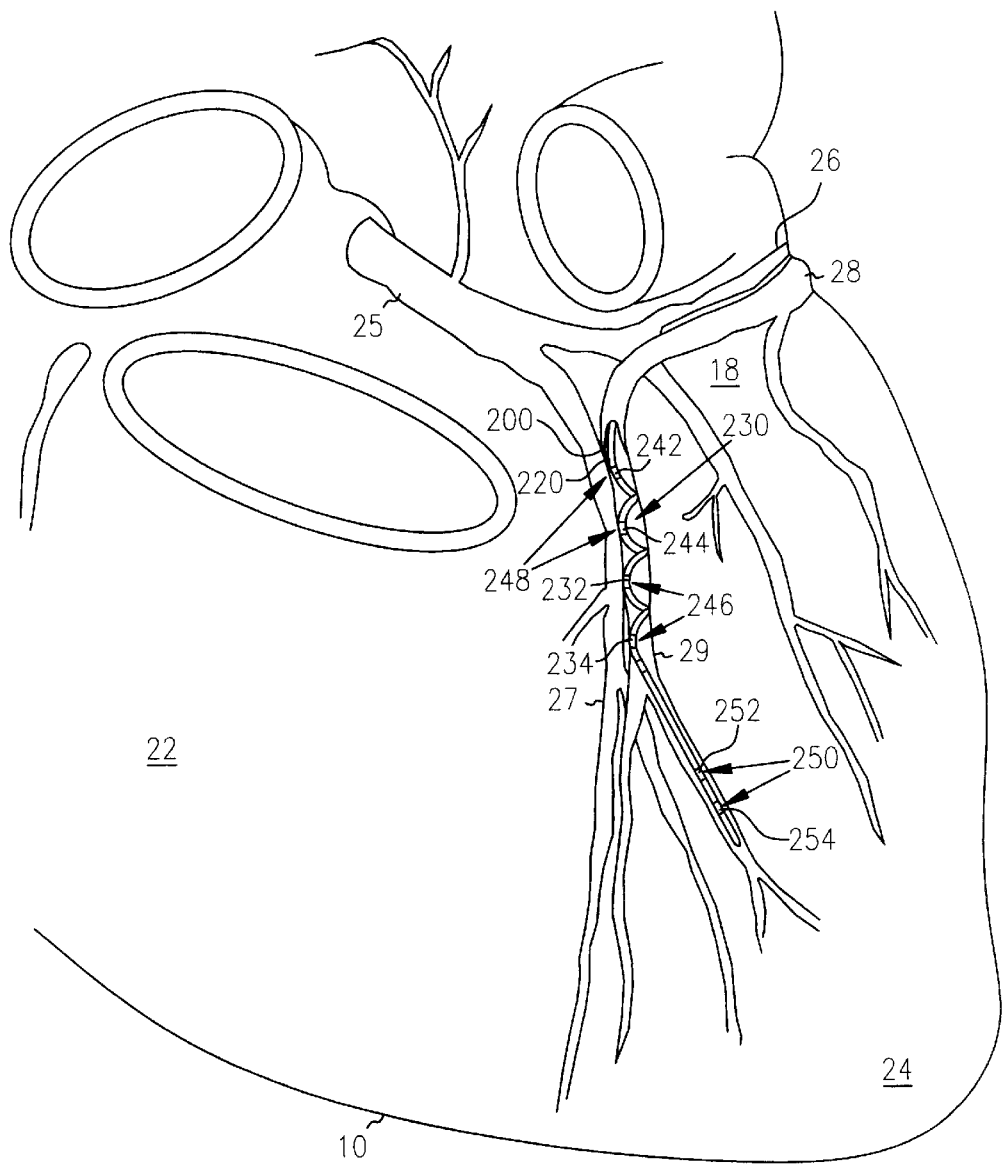
FIG. 3B is side view of a coronary vein lead constructed in accordance with another embodiment, shown positioned in a coronary vein.

Referring to FIG. 3B, the lead 200 is adapted to be used within the coronary artery 25 and also within the coronary branch vein 29. A coronary vein lead 200 with a helical distal portion 230 is shown located in an implanted site. The coronary vein lead 200 includes a mid ventricular electrode pair 246 (electrodes 232 and 234). The electrodes 232, 234 are shown in intimate contact with the vessel wall 108 of the branch vein 29, where the electrodes 232, 234 contact the myocardial wall, as discussed above. The coronary vein lead 200 optionally includes a mid ventricular electrode pair 246 (electrodes 232 and 234) and further optionally includes an apical electrode pair 250 (electrodes 252 and 254). The helical portion 230 and the spacing of the electrodes positions the electrodes 232, 234 against the myocardium to reduce pacing thresholds. The helix diameter is such that a vein of any size will reduce the diameter of the helix so that at least one electrode will be pressed against the myocardial wall. The lead 200 optionally has a fixation mechanism 240, as shown in FIGS. 3A and 3C.

In one embodiment shown at FIG. 3B, multiple smaller electrodes 232, 234, 242, 244 are strategically placed along the helix 230 thereby increasing the probability of direct electrode contact on the myocardial wall of the vein versus the free wall. For example, multiple electrodes are spaced apart along the helix 230 to span from the apex 24 to the base 18 of the heart 10. Electrodes 232, 234 form a midventricular electrode pair 246 and electrodes 242, 244 form a basal electrode pair 248, so designated by their proximity to a particular region of the heart when the lead 200 is in its implanted site in the heart 10. In one embodiment, lead 200 has an apical electrode pair 250 formed of electrodes 252, 254 which have a proximity to the apex 24 of the heart 10 when implanted. The portion of the lead 200 including the apical electrode pair 250 optionally includes a helical portion. In another option, instead of pairs, single electrodes, or more than two electrodes can be included in that discussed above.

In an embodiment where multiple electrodes are connected to the same conductor, the electrode with the best tissue contact will serve as the stimulating electrode. In one embodiment, the lead 200 has multiple electrodes and conductors, and the electrodes which are the cathodes or anodes are selected depending on the thresholds acquired at each stimulation site. As an example, in a bipolar lead, optimal therapy may be achieved by choosing the tip or ring (such as are shown, for example, at 750 and 734 of FIG. 7) as cathode or anode depending on the different thresholds. In the embodiments shown at FIGS. 3A and 3B, multiple electrode capacity is provided in the left ventricular vein. These electrodes are capable of pacing together, or alternatively with only a pair of the electrodes pacing together. Further, the electrodes optionally pace with a delay between them or sequentially.

Figure 3C:
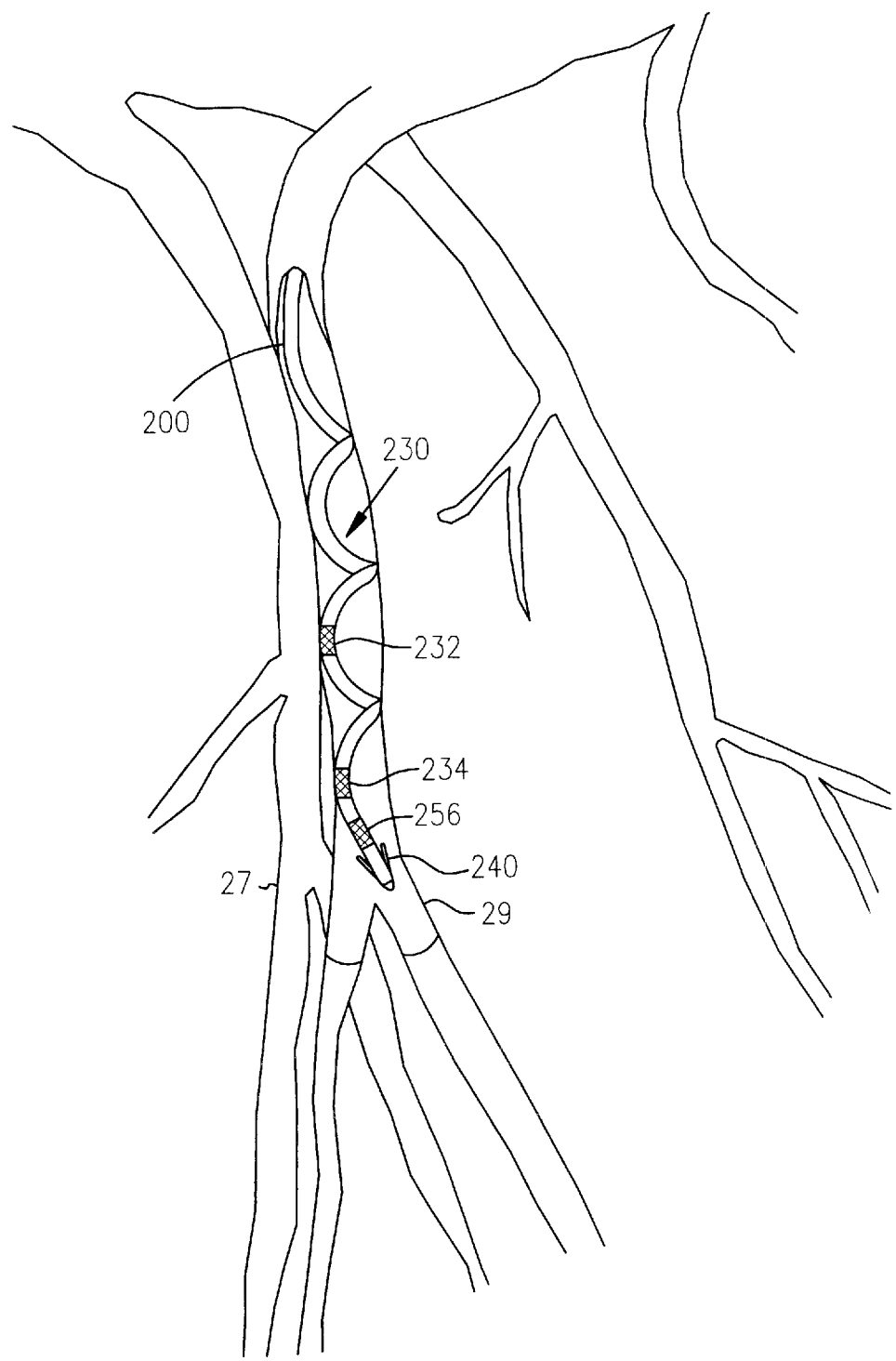
FIG. 3C is side view of a coronary vein lead constructed in accordance with another embodiment, shown positioned in a coronary vein.

Referring to FIG. 3C, a steroid is optionally used to ensure pacing at the cathodal site. The steroid is located in close proximity of the cathode electrode, for example, electrode 234, and not in close proximity of the anode electrode. The steroid is provided by way of steroid collar 256 loaded with the desired drug which is then time released. The steroid collar 256 is external to the lead body 220, and adjacent to the electrode. The drug has a very localized effect, thereby requiring close proximity to the cathode. Steroid release in close proximity to the anode electrode is not critical, but may be allowed. This placement of the steroid collar 256 ensures that the cathode electrode paces first, and before the anode electrode. An example of such a drug is dexamethasone acetate. In another option, a steroid collar or a steroid coating, for example, is provided as a generally cylindrical component adjacent one or both sides of an electrode of any lead described herein.

Another option for the leads described herein involves the use of local drug elution, for example a steroid, in the vicinity of the electrodes. In many applications, desired low chronic pacing thresholds can be achieved through the local release of at least one pharmacologically active agent. This can be easily accomplished by compounding agents into polymeric components positioned adjacent to the electrodes. A pharmaceutical agent typically used in pacing applications is one possessing anti-inflammatory action. Dexamethasone, dexamethasone sodium phosphate and dexamethasone acetate have been used in commercially released devices. Other agents with other actions are other options. For example, steroidal anti-inflammatory agents other than dexamethasone, nonsteriod anti-inflammatory agents, as well as antiarrhythmic, antibiotic, anticoagulative, thrombolytic and other agents known to improve biocompatibility and/or electrical therapies are optionally used.

For steroid release to be therapeutic, it must occur in very close proximity to the electrode. As such, in one embodiment, the steroid is released from the interior of an electrode and subsequently delivered directly to the heart tissue contacting the electrode. This is accomplished by first compounding a biocompatible polymer (such as silicone) with a steroid substance (such as dexamethasone) and then molding the polymer-drug matrix into a small component than can finally be positioned within a porous electrode. Alternatively, a polymer-drug matrix is molded into a generally cylindrical component that can be subsequently positioned adjacent to one or both sides of a generally cylindrical electrode. Another alternative is to apply a thin coating of the polymer-drug matrix to the completed lead body construction in locations consistent with the needed close proximity to the electrode. In yet another option, a steroid collar is used, as discussed above.

Figure 4A:
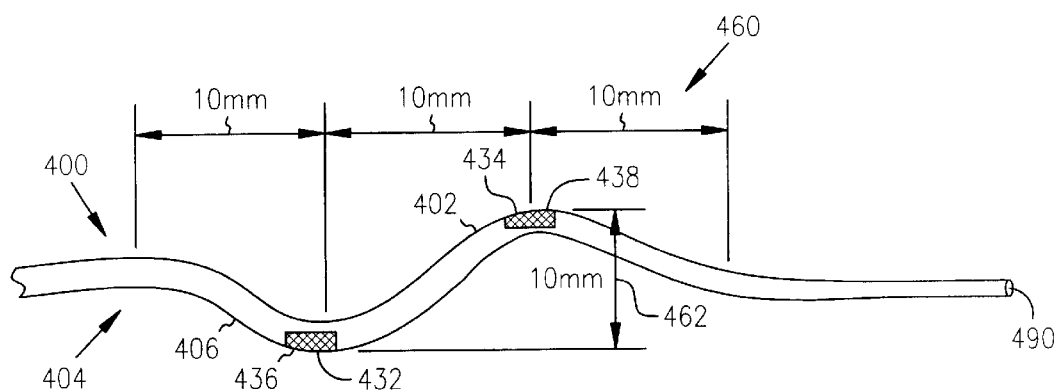
FIG. 4A is a side view of a coronary vein lead constructed in accordance with one embodiment.

In one embodiment, the lead is constructed and arranged for fixation in the coronary sinus and has specific biases to facilitate placement and retention in the coronary sinus. Referring now to FIGS. 4A, a double-bias lead 400 constructed and arranged for fixation in the coronary sinus is shown. It should be noted that the double-bias lead 400 can be combined with embodiments discussed above and below. The lead 400 includes a first bias 402 and a second bias 406, although an additional bias is optionally further provided with the lead 400. The first bias 402 is disposed in a direction that is different than the second bias 406.

Figure 4B:
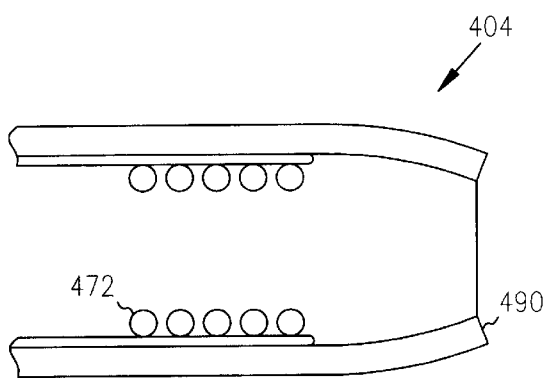
FIG. 4B is a side view of a coronary vein lead constructed in accordance with one embodiment
Figure 4C:
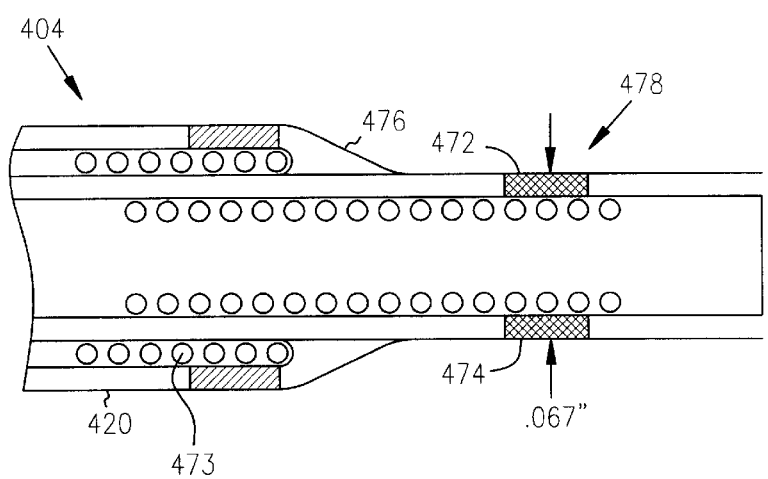
FIG. 4C is a side view of a coronary vein lead constructed in accordance with one embodiment

At FIG. 4A, a lead 400 is shown include half ring electrodes 432, 434 which are biased against the vessel wall by a biased portion 460 of the lead 400. In one embodiment, the electrodes 432, 434 are spaced about 10 mm apart along the lead 400, and the length of the biased portion 460 is about 30 mm. In one embodiment, the lead 400 is constructed and arranged so a first plane including a surface 438 of the electrode 434 is spaced about 10 mm from a second plane including a surface 436 of the electrode 432. The lead 400 in one embodiment is an over the wire lead with an open distal end, as shown in FIG. 4B. A distal portion 404 near distal end 490 has a diameter of about 0.66 inch (5 French).

Figure 4D:
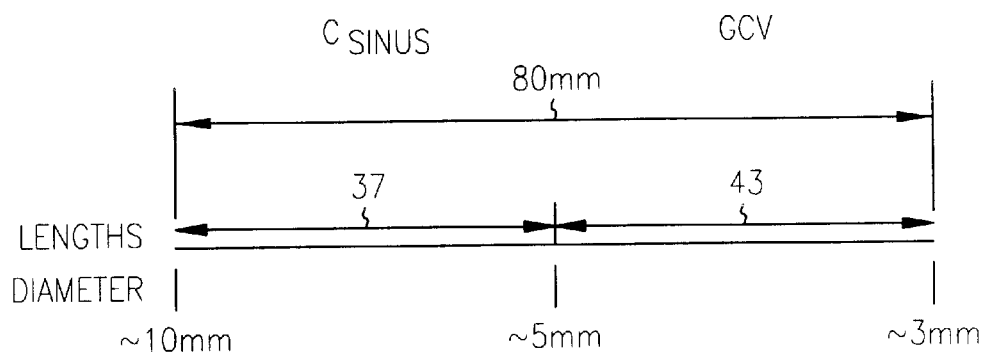
FIG. 4D shows lengths and diameters of a coronary vein lead constructed in accordance with one embodiment.
Figure 4E:
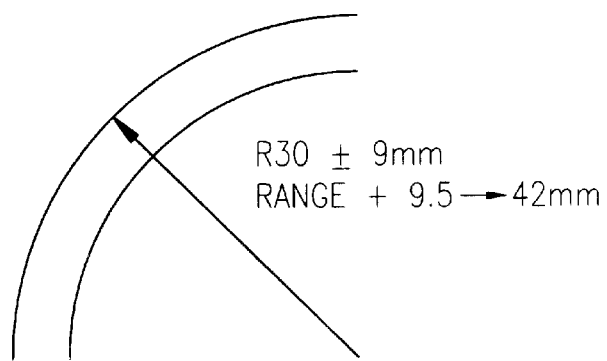
FIG. 4E shows radii of a coronary vein lead constructed in accordance with one embodiment; vein geometry

The lead 400 has a length which fits within the coronary sinus/great cardiac vein. The bias portion 460 pushes the electrode up against the vein wall. The bias portion 460 is constructed and arranged to fit within the area of the coronary sinus/great cardiac vein around the mitral valve. The lengths and diameters of the coronary sinus/great cardiac vein are shown at FIG. 4D. The coronary sinus has a length of about 37 mm and the great cardiac vein has a length of about 43 mm, for a combined length of about 80 mm. The diameter of the proximal end of the coronary sinus at the thebesian valve is about 10 mm. Where the coronary sinus and the great cardiac vein meet at the distal end of the coronary sinus and the proximal end of the great cardiac vein at the valve of vieussens, the diameter is about 5 mm. The distal portion of the great cardiac vein has a diameter of about 3 mm.

The mitral valve may have a radius (R) between about 9.5 mm–42 mm. In general the radius is about 30 mm. In one embodiment, the biased lead portion 460 shown at FIG. 4A has a radius between about 9.5 mm to about 42 mm. In one embodiment, the biased portion has a radius of about 30 mm.

The biased portion 460 of lead 400 urges electrodes 432,434 against the vein wall. The diameter of the bias portion 460 of lead 400 is between electrodes 432 and 434 is larger than the diameter of the vein to provide a snug fit. In one embodiment the diameter is about 10 mm. Subtle lateral forces on vessel wall produce reliable long term stability. Lateral forces between electrode and vessel wall result in low pacing thresholds. In one embodiment, the distal end of the lead 400 has a diameter of about 0.066".

Referring to FIG. 4B, in one embodiment the lead 400 has an atraumatic tip 490 having an outer diameter of about 5 French (0.066 inch) and an inner diameter of about 0.038 inch. The interior space between coils 472 has a diameter of about 0.018 inch. Atraumatic tip 490 in one embodiment comprises silastic tubing extending beyond the coils 472 to avoid bruising the vasculature during implantation therein. At FIG. 4C the transition 476 from a portion of lead body 420 which has two coils to the distal portion having one coil 478 is shown. In one embodiment, the distal portion having one coil 478 has an outer diameter of about 0.066 inch. In one embodiment the distal portion 404 has a ring electrode 474. In one embodiment the lead has an outer diameter of about 0.067 inch at the point where electrode 474 is located.

Because the lead 400 of FIG. 4A is designed to be implanted inside the coronary sinus/great cardiac veins (CS/GCV), the size of the lead in relation to the veins is very important. The leads described herein are designed to be held in place by wall tension, i.e. by the force of the lead against the heart wall. The lead 400 must be small enough to slide into place and not damage the walls by excess forces. The lead bias or holding mechanism must not be too small or the lead 400 may become dislodged and fall out. The biased portion 460 must not be too long or it will extend into the atrium. Referring to FIG. 4D, the length of the coronary sinus and great cardiac veins together is 80 mm. If the pacing electrodes are desired to sit in the middle of that vein when the tip 470 of the lead 400 is located at the end of the great cardiac veins, the electrode should be placed about 43 mm proximal to the tip. The diameter of the vein averages at 10 mm at the os (entrance) and goes down to an average of 3 mm at the end of the great cardiac veins. As such, the intended position in the implanted site, or the final lead position, is considered in the lead design so that in its final position the lead 400 is wedged or held in the appropriate place. The outer diameter of the portion that is being wedged in place would be about 20 to 30% larger than the inner diameter of the blood vessel. For example, referring to FIG. 4A, the dimension 462 of the biased portion 460 is 10 mm. This would wedge into a portion of the vein that is about 7 mm in diameter, which is near the end of the coronary sinus near the beginning of the great cardiac veins.

In one embodiment, the lead body 420 may be made of a biocompatible material having shape memory characteristics such that it will return to its preformed shape once implanted and a stylet or guidewire is removed. An example of such a material is polyether polyurethane. In addition, the lead body may have portions which have shape memory characteristics, comprising either a shape memory polymer or a shape memory metal.

FIGS. 5A–5D show a lead 500 constructed and arranged for fixation in the coronary sinus, where the lead 500 includes any of the above and below discussed leads. The silicone arches 540, in one option, are attached to and extend from a lead body 520 opposite the contact area 536 of electrode 532. The arches 540 provide spring forces to position the electrode 532 against the vessel wall, and help to reduce dislodgement and keep pacing thresholds lower.

The arches 540 also reduce complications arising in the event that the lead 500 must be removed. Referring to FIG. 5C, in one option, the arch or arches 540 are part of a molded part of the lead 500. In another option, as shown at FIG. 5D, the arches 540 are straight silicone rubber cylinders affixed to the lead body 520 wall by glue in two locations that force the cylinders to assume an arched configuration. Alternatively, molded components in the shape of an arch are positioned on the lead body 520, as shown at FIGS. 5A and 5B.

The arches 540 straddle the electrode 532, as shown in FIGS. 5A, 5C, and 5D. In operation, any of the above mentioned arches 540 provide a side thrust to the lead body 520 when that lead body 520 is advanced into a narrow vessel with an inner diameter less than the combined distance of the lead body outer diameter (d, as shown at FIG. 5B) and the maximum height (h, as shown at FIG. 5B) of the arch. The side thrust will force the electrode 532 against the vessel wall in a position opposite of the arches 540. These arches 540 are provided to reduce the rate of two types of complications. First, during implantation of a lead body 520 having arches 540, that lead body 520 could be manipulated back and forth in the vessel. Second, and consistent with the first advantage, repositioning or removal of a subchronic or chronic lead will be easier than if the lead had free ended springs (like tines) entangling tissues when manipulation in at least one direction is needed. In an alternative embodiment, the lead 500 also comprises a helical portion as shown at FIGS. 1–2 and 3A–3C. In one embodiment, the lead body 520 may be made of a biocompatible material having shape memory characteristics such that it will return to its preformed shape once implanted and a stylet or guidewire is removed. An example of such a material is polyether polyurethane. In addition, the lead body may have portions which have shape memory characteristics, comprising either a shape memory polymer or a shape memory metal.

Figure 6A:
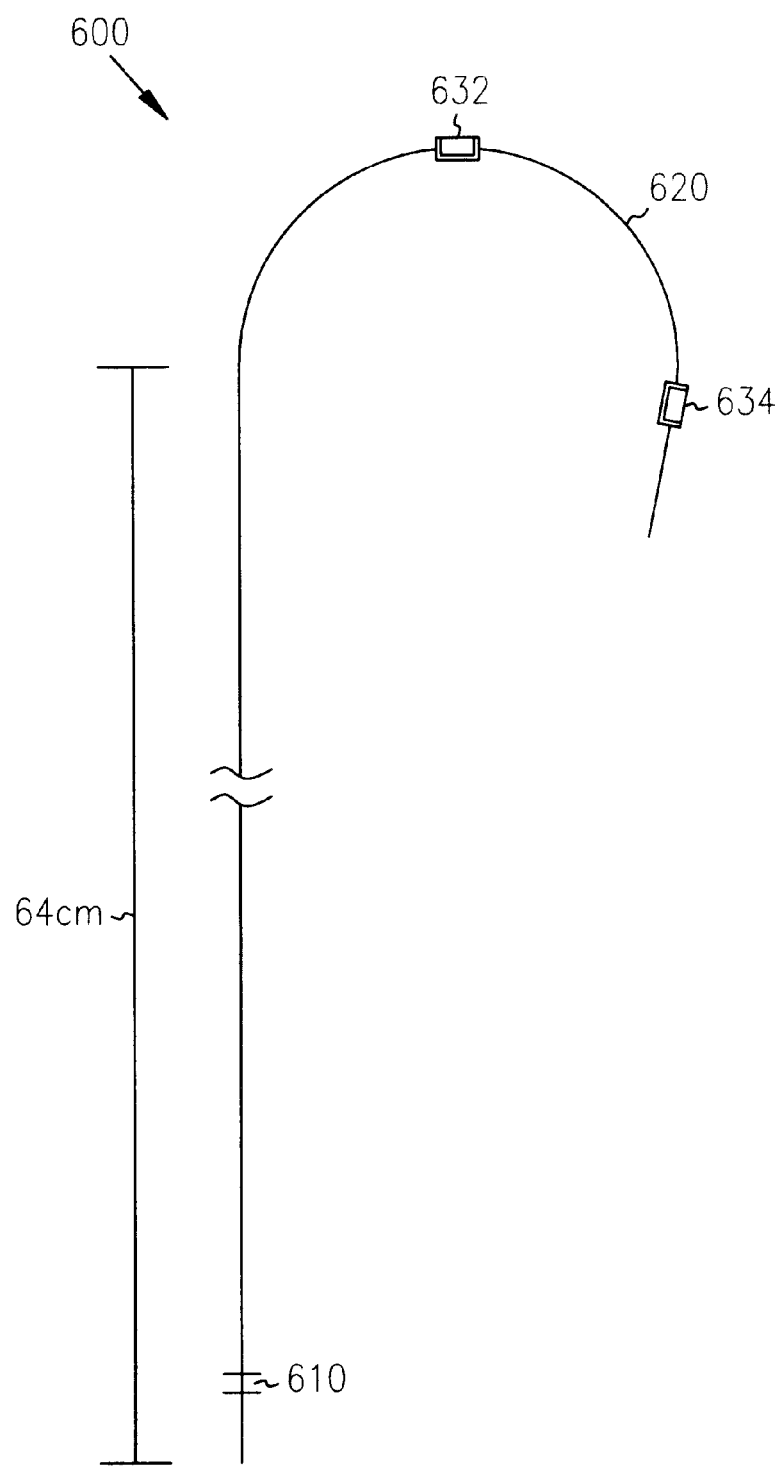
FIG. 6A is a side view of a coronary vein lead constructed in accordance with one embodiment.
Figure 6B:
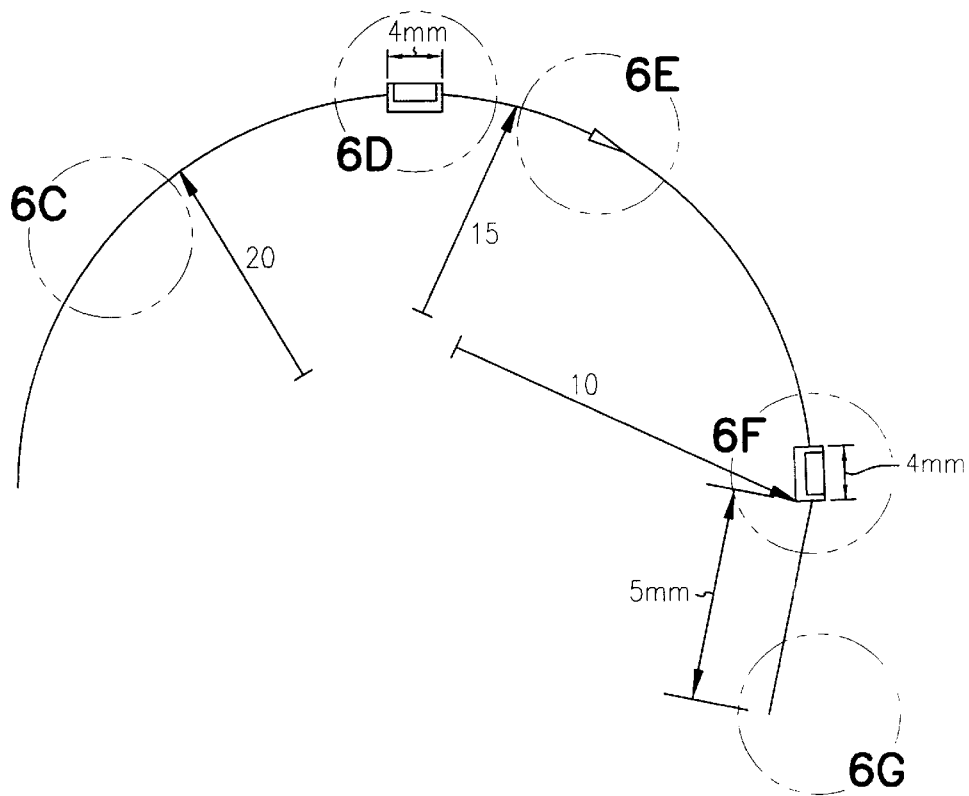
FIG. 6B is a side view of a coronary vein lead constructed in accordance with one embodiment.

FIGS. 6A–6G show a lead 600 adapted for implantation and fixation in the coronary sinus. FIG. 6A shows the entire lead 600, and FIGS. 6B–6G illustrate a portion of the lead 600. The lead body 620 is generally shaped with the same or smaller radius of curvature as the coronary sinus, so that it hugs the anatomy of the coronary sinus when the lead 600 is implanted. The shape of the lead body 620 hugging the myocardial wall of the coronary sinus urges the electrodes 632, 634 against the wall of the coronary sinus. Because of this geometry compatibility, the lead 600 will have good long term stability with relatively small forces on the lead body 620 and vessel walls. By distributing forces along the extent of the lead body 620, the possibility of lead or vessel wall damage is reduced. FIG. 6B shows the distal portion of one embodiment of lead 600 in greater detail.

The radii of curvature and angles along different portions of the lead body are shown. In one option, the lead body 620 is made of a biocompatible material having shape memory characteristics such that it will return to its preformed shape once implanted and a stylet or guidewire is removed. An example of such a material is polyether polyurethane. In addition, the lead body may have portions which have shape memory characteristics, comprising either a shape memory polymer or a shape memory metal. In another option, the lead body 620 is preformed such that is has a shape adapted to hug the heart while the lead 600 is disposed in the coronary sinus. It should be noted that the hugging shape of the lead body 620 can be combined with any of the above and below discussed embodiments.

Figure 6C:
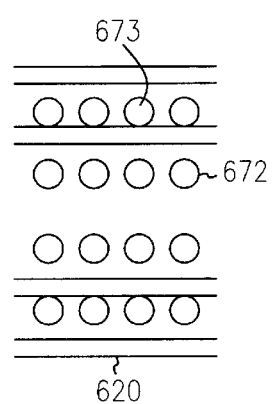
FIG. 6C is an enlarged cross section of a portion of the lead as shown in FIG. 6B.
Figure 6D:
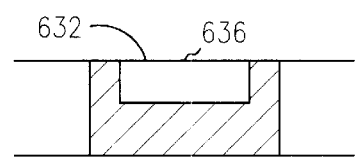
FIG. 6D is an enlarged cross section of a portion of the lead as shown in FIG. 6B.
Figure 6E:
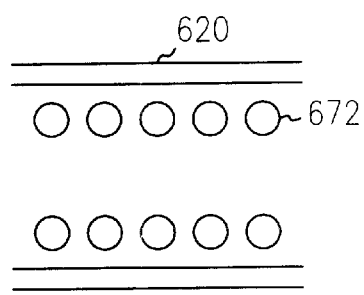
FIG. 6E is an enlarged cross section of a portion of the lead as shown in FIG. 6B.
Figure 6F:
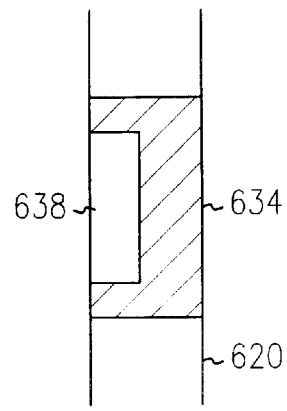
FIG. 6F is an enlarged cross section of a portion of the lead as shown in FIG. 6B.
Figure 6G:
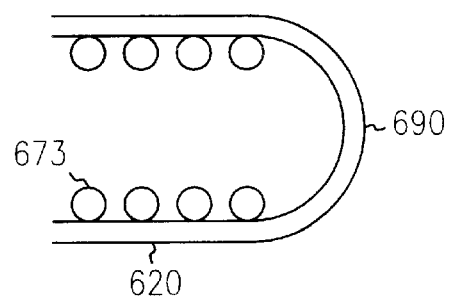
FIG. 6G is an enlarged cross section of a portion of the lead as shown in FIG. 6B.

FIG. 6C shows the side cross section of one embodiment of the lead 600 along line C—C of FIG. 6B. The lead 600 optionally has two sets of coils 672,673 at this portion. FIG. 6D shows a pacing electrode 632 in greater detail. The electrode 632 optionally is partially masked with the contact portion 636 facing outward, so that in an implanted site, the electrode 632 contacts the vascular tissue adjacent the myocardial wall. FIG. 6E shows the side cross section of the lead along line E—E of FIG. 6B, of a lead portion having one set of coils 672. FIG. 6F shows one embodiment of electrode 634 in greater detail, showing a partially masked electrode 634 with the contact portion 638 facing inward. FIG. 6G shows the side cross section of the lead 600 along line G—G of FIG. 6B showing the end tip 690 of the lead 600.

Figure 7:
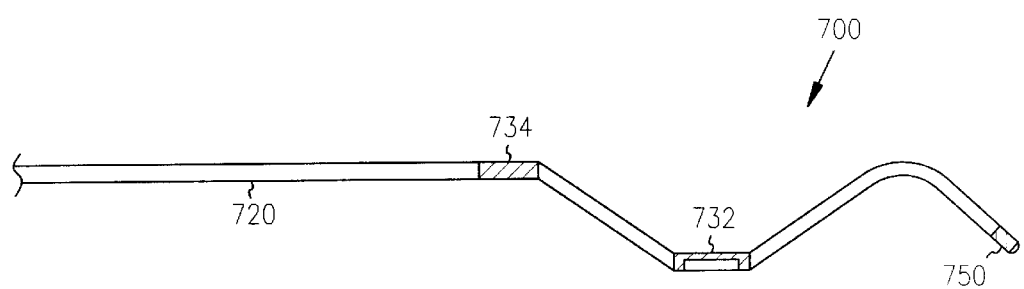
FIG. 7 is a side view of a coronary vein lead constructed in accordance with one embodiment.

FIG. 7 illustrates another option for a cardiac vein lead, for example, a multiple polar lead 700 adapted for use in a cardiac vein. In one option, a third electrode 750 is added to a bipolar configuration, and the lead 700 can be used to pace and sense both the atrium and the ventricle. This configuration would allow the middle electrode 732 to be used as a common anode for both an atrial and ventricular bipole. This configuration would result in a lead utilizing the advantages of two bipole pairs with only three electrodes. In another option, the electrode 734 is electrically common with the electrode 750.

The lead 700 has a proximal end (as shown at 102 of FIG. 1), and attaches to a pulse sensor and generator (as shown at 140 of FIG. 1). The lead body 720 is cylindrical in shape and includes one or more electrical conductors. The electrical conductors are made of a highly conductive, highly corrosion-resistant material. The one or more electrical conductors carry current and signals between the pulse sensor and generator and the electrodes 732, 734 and 750. In one embodiment, the electrode 734, for example, a full ring electrode, serves as ground. The electrode 732 is a half ring electrode and serves as an atrial electrode. In another option, the electrode 750 is a PICOTIP (TM) electrode, and also comprises a ventricular electrode.

Figure 8:
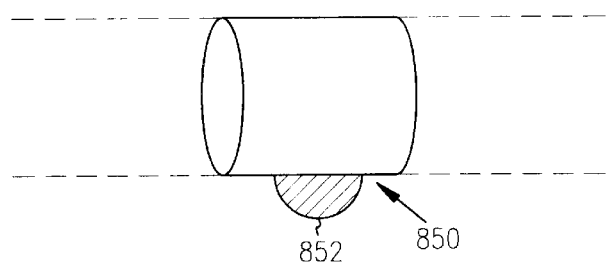
FIG. 8 is a side view of an electrode constructed in accordance with one embodiment of the coronary vein lead.

FIG. 8 shows a miniaturized high impedance PICOTIP (TM) electrode 850 constructed and arranged to be a side mounted electrode, which can be used with any of the leads discussed herein. This miniaturized electrode 850 increases electrode impedance by using a smaller exposed area. Electrode 850 comprises an electrode mesh 852 which increases chronic lead stability by providing local tissue ingrowth into the electrode mesh. In another embodiment, the PICOTIP (TM) electrode protrudes from the lead body to enhance intimate wall contact.

A lead according to the coronary vein leads described herein is implanted in any suitable;manner, for example, as follows. Venous access is obtained via the subclavian, cephalic or jugular vein. A standard stylet is inserted into the lead to straighten it and provide stiffness for insertion of the lead into the vasculature. The coronary vein lead will then be guided into the coronary sinus/great cardiac vein. Once the coronary vein lead is positioned, the stylet will be removed. The preferred position for coronary vein lead placement is, in one option, to place the tip of the coronary vein lead near the origin of the great cardiac vein just proximal to the point where it originates from the interventricular vein. This will position the pacing electrodes near the end of the coronary sinus.

The lead is tested for P-wave, P/R ratio and atrial and ventricular threshold. The lead will be manipulated and repositioned to maximize P-Wave and P/R ratios, and minimize atrial voltage threshold. Target thresholds will be below 2.0 volts with a P-wave above 2 mVolts and a P/R ratio above 2. An optional method for implanting these leads is to use an "over the wire" method. This involves (1) placing a guide catheter into the coronary sinus (2) threading a guide wire into the coronary veins, and (3) pushing the lead over the guide wire.

Figure 9:
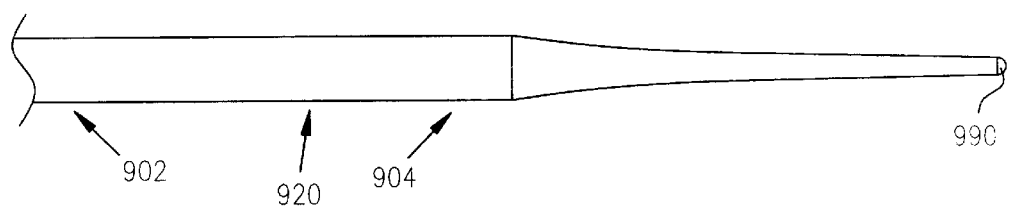
FIG. 9 is a side view of a coronary vein lead constructed in accordance with one embodiment.

Two other design features are described herein which improve the implantability and the chronic performance of leads. First, it was found that a slender distal tubing or stylet/conductor coil section was instrumental in improving the ability of the medical personnel to position these leads. It is believed that this feature provided the distal portion of the lead with a guiding means that easily followed the vasculature. This was accomplished only when the diameter of this guiding section was considerably less than that of the vasculature. In one embodiment shown at FIG. 9, a lead body 920 having a tapered flexible distal tip 990 at its distal end 904 is shown which allows for easier access to distal veins. The outer diameter 980 of the lead body 920 tapers from the proximal portion 902 to the distal end 990 of the distal portion 904. The tapered lead body provides a smaller outer diameter at the distal end 990, and allows more easy access to the distal veins, which have a decreasing inner diameter, and can be more complex.

Figure 10A:
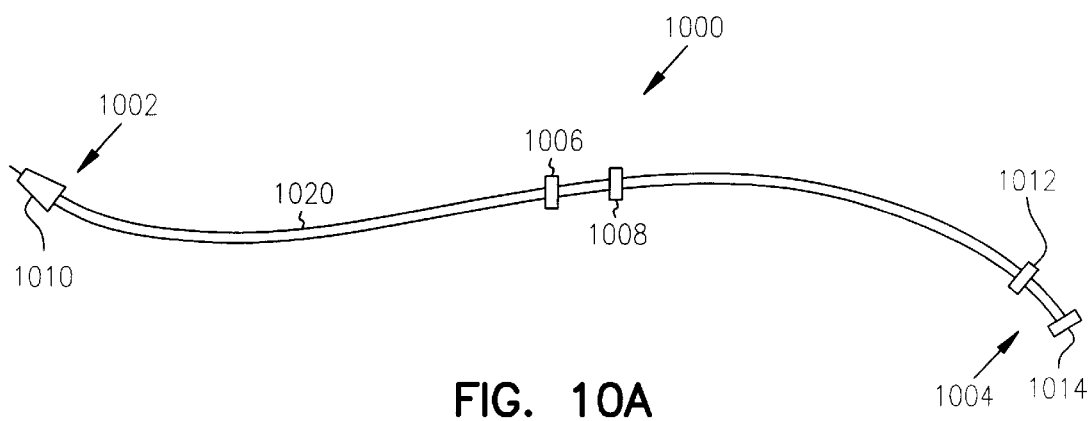
FIG. 10A is a side view of a coronary vein lead constructed in accordance with one embodiment.

Referring to FIG. 10A, a lead is shown generally at 1000. The lead 1000 provides ventricular, pacing and sensing with or without atrial pacing and sensing. In another option, the lead 1000 provides atrial pacing and sensing with or without ventricular pacing and sensing. In yet another option, the lead 1000 provides ventricular pacing and sensing with or without sided defibrillation. The lead 1000 has a proximal end shown generally at 1002 and a distal end shown generally at 1004. The lead 1000 has a connector terminal 1010 at its proximal end and a lead body 1020, and is constructed and arranged for insertion into the coronary sinus. The lead 1000 attaches to a pulse sensor and generator 1040. The lead body 1020 has multiple electrodes. Proximal ring electrodes 1006 and 1008 are provided for atrial or ventricular sensing and distal electrodes 1012 and 1014 are provided for ventricular sensing and pacing. Connector terminal 1010 electrically connects the various electrodes and conductors within the lead body to the pulse sensor and generator 1040. The pulse sensor and generator 1040 also contains electronics to sense various pulses of the heart and also produce pulsing signals for delivery to the heart. The pulse sensor and generator 1040 also contains electronics and software necessary to detect certain types arrhythmias and to correct for them. Physicians are able to program the pulse sensor and generator to correct a particular arrhythmia that the patient may have. It should be noted that there are numerous types of connector terminals which connect to a pulse sensing and generating unit 1040.

In use, the distal end 1004 of the lead 1000 is placed far enough into the coronary venous system to stimulate the ventricle, as shown for example, in FIG. 3B. This stimulation may occur at the base of the ventricle, the middle ventricle or the apex of the ventricle.

Figure 10B:
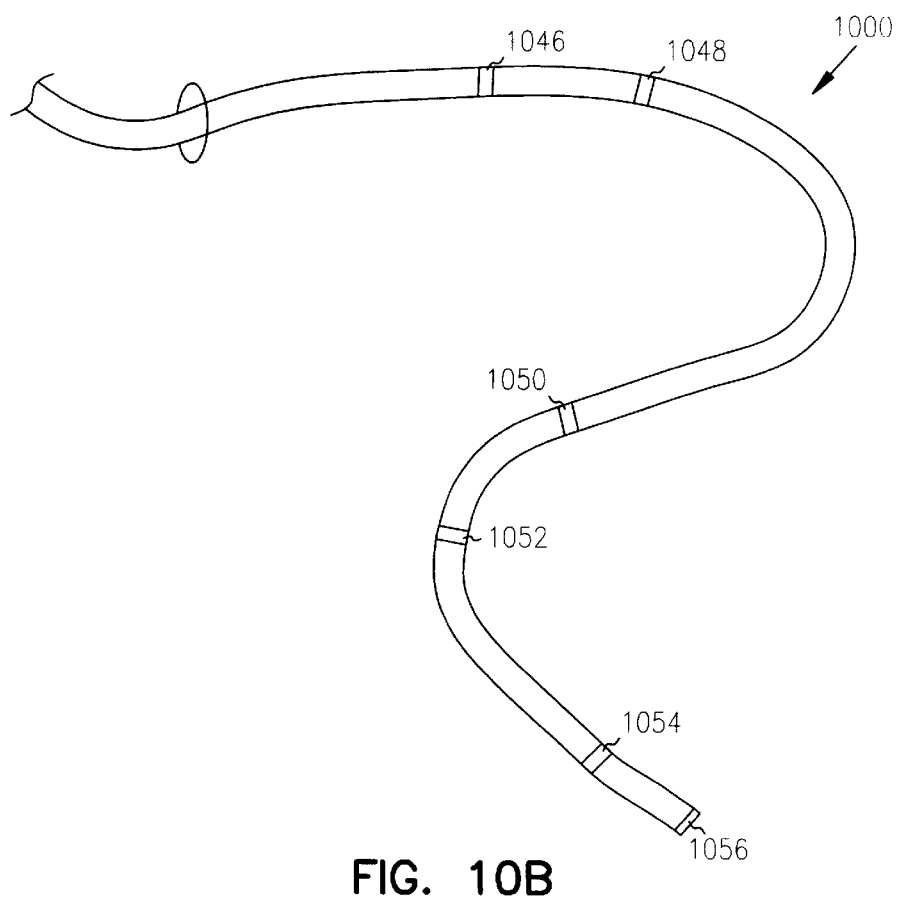
FIG. 10B is a side view of a coronary vein lead constructed in accordance with one embodiment.

In one embodiment, the lead 1000 is implanted only for pacing and sensing purposes, and the lead 1000 may have a unipolar or bipolar distal electrodes. Referring to FIG. 10B, in one embodiment, the lead 1000 has multiple pairs of distal electrodes for multisite ventricular pacing. Electrodes 1046 and 1048 form an electrode pair located in the coronary sinus/great cardiac vein, and electrodes 1050 and 1052 form an electrode pair located in the ventricular portion of the lead 1000, implanted in the coronary venous system. Electrodes 1054 and 1056 also form an electrode pair located on the ventricular portion of the lead 1000 implanted in the coronary venous system. The embodiment shown at FIG. 10B may have a lead body 420 made of a biocompatible material having shape memory characteristics such that it will return to its preformed shape once implanted and a stylet or guidewire is removed. An example of such a material is polyether polyurethane. In addition, the lead body may have portions which have shape memory characteristics, comprising either a shape memory polymer or a shape memory metal.

In one embodiment, the lead 1000 has proximal electrodes, shown at 1006 and 1008 of FIG. 10A, which are either bipolar or unipolar, for sensing and/or pacing of the atrium. In one embodiment, multiple pairs or multiple sets of electrodes may be used for bi-atrial pacing. An optional distal electrode 1014 of the lead 1000 serves as a distal shocking electrode for the purpose of delivering a high energy shock greater than about 0.01 Joule to the ventricle. This distal shocking electrode may be added to any of the lead configurations disclosed herein.

The leads described herein provide several advantages over previous leads. The leads provide, in one option, the ability to sense and pace the heart using leads positioned within the cardiac vasculature, and further the leads provide the ability to pace and/or sense the left heart. It has been found that by placing a therapeutic lead near the atrium, but not in the atrium, higher amplitude electrograms may be detected as compared to a standard endocardial lead. Further, it has been found that left sided pacing may help suppress atrial arrhythmias, particularly those originating near the left atrium. Still further, it has been found that the ability to critically control the timing between pacing the atria and ventricles of the heart is of utility in optimizing pacing therapies. The leads described herein involve geometries that utilize the shape of the local vasculature, the shape of the heart, or both, to help insure that an optimally positioned lead will remain in that position well beyond the time of implant. The lead designs discussed herein yield reliable and optimal performance in sensing and pacing of the heart. New coronary lead configurations are provided which can provide dual chamber pacing and/or defibrillation on a single lead body.

Further provided herein is a method for placing a lead into a coronary vein to provide sensing and pacing of the heart, for example, the left side of the heart. In one embodiment, a lead is provided that is a right side lead and is placed within the coronary sinus, and is then advanced from the coronary sinus toward the left atrium to provide left sided sensing and pacing.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A lead comprising:
    a lead body adapted to carry signals to and from a heart, the lead body having a proximal portion and a distal portion;
    a connector located at a proximal end of the lead, the lead adapted for connection to a signal generator, the lead constructed and arranged for implantation within a coronary vein, the distal portion of the lead body having a helical portion adapted to be implanted within the coronary vein; and at least one electrode coupled with the helical portion of the lead body; and a plurality of electrodes are disposed on the helical portion, and the plurality of electrodes are spaced about 120 degrees apart along the helical portion.

2. A lead comprising:

a lead body adapted to carry signals to and from a heart, the lead body having a proximal portion and a distal portion;

a connector located at a proximal end of the lead, the lead adapted for connection to a signal generator, the lead constructed and arranged for implantation within a coronary vein, the distal portion of the lead body having a helical portion adapted to be implanted within the coronary vein; and at least one electrode coupled with the helical portion of the lead body; and apical electrodes, mid ventricular electrodes, and ventricular electrodes on the helical portion.

3. A method for inserting a coronary vein lead into a coronary vein, the method comprising:

providing the coronary vein lead including:

a lead body adapted to carry signals to and from a heart, the lead body having a proximal portion and a distal portion, and an intermediate portion therebetween;

a connector located at a proximal end of the lead, the lead adapted for connection to a signal generator for monitoring or stimulating cardiac activity, the distal portion of the lead body constructed and arranged to hug an interior wall of the coronary vein upon implantation;

the distal portion of the lead body having a tapered outer diameter, and the outer diameter of the distal portion includes a first diameter that is equal to a diameter of the intermediate portion;

a first electrode associated with the distal portion of the lead body, the first electrode including a first electrode contact area; and a second electrode associated with the distal portion of the lead body, the second electrode including a second electrode contact area, the first and second electrodes upon implantation in a body being housed in the coronary vein;

inserting the coronary vein lead into a coronary sinus;

sensing and pacing the heart via the coronary vein lead in its implanted site in the coronary vein; and providing the distal portion of the lead with a helical configuration, and urging the first and second electrodes toward the wall of the coronary vein.

4. The method as recited in claim 3, further comprising advancing the lead from the coronary sinus toward a left atrium and into a coronary branch vein.

5. The method as recited in claim 4, wherein sensing and pacing comprises providing pacing and sensing of a left ventricle.

6. The method as recited in claim 3, further comprising rotating the lead while inserting the lead in the coronary sinus.

* * * * *